(12) United States Patent
Zeroug (10) Patent No.: US 6,483,777 B1
(45) Date of Patent: Nov. 19, 2002

(54) METHOD AND APPARATUS FOR ULTRASONIC IMAGING OF A CASED WELL

(75) Inventor: Smaine Zeroug, Ridgefield, CT (US)

(73) Assignee: Schlumberger Technology Corporation, Ridgefield, CT (US)

( * ) Notice: Subject to any disclaimer, the term of this patent is extended or adjusted under 35 U.S.C. 154(b) by 0 days.

(21) Appl. No.: 09/581,701
(22) PCT Filed: Jan. 6, 1999
(86) PCT No.: PCT/US99/00207
    § 371 (c)(1),
    (2), (4) Date: Jul. 14, 2000
(87) PCT Pub. No.: WO99/35490
    PCT Pub. Date: Jul. 15, 1999

Related U.S. Application Data

(60) Provisional application No. 60/070,531, filed on Jan. 6, 1998.

(51) Int. Cl.[7] .................................................. G01V 1/40
(52) U.S. Cl. ........................................................ 367/35
(58) Field of Search ........................ 367/35; 73/152.54; 181/105

(56) References Cited

U.S. PATENT DOCUMENTS

| | | |
|---|---|---|
| 2,538,114 A | 1/1951 | Mason ........................... 73/67 |
| 3,401,773 A | 9/1968 | Synnott, III ..................... 181/5 |
| 4,255,798 A | 3/1981 | Havira ........................... 367/35 |
| 4,779,236 A | 10/1988 | Sondergeld ..................... 367/31 |
| 4,813,028 A | 3/1989 | Liu .............................. 367/31 |
| 5,001,676 A | 3/1991 | Broding ......................... 367/31 |
| 5,168,470 A | 12/1992 | Dennis et al. .................. 367/31 |
| 5,357,481 A | 10/1994 | Lester et al. ................... 367/31 |
| 5,763,773 A | 6/1998 | Birchak et al. .............. 73/152.58 |
| 5,859,811 A | 1/1999 | Miller et al. ................... 367/35 |

FOREIGN PATENT DOCUMENTS

| | | | |
|---|---|---|---|
| EP | 0 549 419 A2 | 6/1993 | ............ G01V/1/40 |
| EP | 0 549 419 B1 | 1/1997 | ............ G01V/1/40 |
| EP | 0 837 217 A2 | 4/1998 | ........... E21B/47/00 |
| GB | 2 292 799 A | 3/1996 | ............ G01V/1/48 |

Primary Examiner—Gregory J. Toatley, Jr.
(74) Attorney, Agent, or Firm—William B. Batzer; John J. Ryberg (57) ABSTRACT

A method and apparatus for utilizing flexural excitations to characterize and/or image a cased well is disclosed. Various applications of the method and apparatus are also discussed.

60 Claims, 3 Drawing Sheets

METHOD AND APPARATUS FOR ULTRASONIC IMAGING OF A CASED WELL

CROSS-REFERENCE TO RELATED APPLICATION

The present application is related to, and claims priority of, U.S. patent application Ser. No. 60/070,531, filed Jan. 6, 1998, METHOD AND APPARATUS FOR FLEXURAL WAVE IMAGING OF CASED WELLS, the entire content of which is hereby incorporated by reference herein.

BACKGROUND OF THE INVENTION

1. Field of the Invention

The present invention relates generally to methods and apparatus for ultrasonically imaging cased wells. More specifically, the invention relates to methods and apparatus for imaging and characterizing, with azimuthal resolution, (i) the annular region between the casing and the earth formations surrounding the casing and (ii) the wall surface of such earth formations.

2. Description of the Prior Art

In a well completion, a string of casing or pipe is set in a wellbore, and a fill material (typically cement) is forced into the annulus between the casing and the earth formations. The primary purpose of such cement is to separate oil- and gas-producing layers from each other, and from water-bearing strata.

If the cement fails to provide isolation of one zone from another, fluids under pressure may migrate from one zone to another, reducing production efficiency. In particular, migration of water into a hydrocarbon-bearing zone can, in some circumstances, render a well non-commercial. Also, migration of hydrocarbons into aquifers is environmentally and economically undesirable. Thus, imaging the annulus content, and, in particular, detecting interfaces between cement and a fluid-channel and/or between cement and the formation, is important for reliable determination of the hydraulic isolation of the different strata of a formation.

Current open-hole logging procedures—using electrical devices, such as Schlumberger's Fullbore Formation Micro-Imager (FMI), or acoustic devices, such as Schlumberger's Ultrasonic Borehole Imager (UBI)—stress the importance of imaging the formation wall. These imaging techniques allow for identification of hydrocarbon-bearing beds within the earth formations, and for detection of fractures, breakouts, and washouts, to help assess well stability; however, they do not work through casing.

It is widely reported that a significant percentage of existing cased wells were never imaged prior to encasement. There may be several reasons why such wells were never imaged prior to encasement, e.g., lack of adequate imaging technology, cost, etc. Today, however, imaging of existing cased wells can be desirable for, among other things, detection and identification of so-called bypassed pay (i.e., hydrocarbon-bearing) zones.

Another need for through-the-casing imaging exists in the process of hydraulic fracturing, which typically takes place after a well has been cased, and is used to stimulate the well for production. Often, the fracturing process is accompanied by sanding, whereby certain strata of the formation release fine sand that flows through casing perforations into the well, and then up to the surface, where it can damage production equipment. This problem can be remedied if the sand-producing zones are detected—as could be done, for example, with an imaging technology capable of operating through the casing.

Generally speaking, a cased well includes a number of interfaces at the junctures of the differing materials within the wellbore. A "first interface" exists at the juncture of the borehole fluid in the casing and the casing. (The casing is generally referred to as a "first material" and is typically comprised of steel.) A "second interface" is formed between the casing and a second material adjacent to the exterior of the casing. If cement is properly placed in the annulus, the "second interface" exists between the casing (i.e., the first material) and the cement (i.e., the second material). A "third interface" also exists between the cement and a "third material" (i.e., the formation).

The problem of investigating the fill material within the annulus has motivated a variety of cement evaluation techniques using acoustic energy. These techniques generally fall into two classes: (i) sonic cement evaluation and (ii) ultrasonic cement evaluation.

One sonic cement evaluation technique, described in U.S. Pat. No. 3,401,773, to Synott, et al., uses a logging tool employing a conventional, longitudinally spaced sonic transmitter and receiver. The received signal is processed to extract the portion affected by the presence or absence of cement. The extracted portion is then analyzed to provide a measurement of its energy, as an indication of the presence or absence of cement outside the casing. This technique provides useful information about cement detects at the second interface. However, sonic techniques have several limitations, such as: (i) poor azimuthal and axial resolutions, and (ii) strong sensitivity to the bond quality between the casing and the cement, thus requiring, in the cases of poor bond quality, internal pressurization of the casing, which, itself, can degrade cement integrity.

Ultrasonic cement evaluation tools, such as Schlumberger's Cement Evaluation Tool (CET) and UltraSonic Imager (USI) Tool, concentrate on the second interface to determine whether cement or mud is adjacent to the casing. in the annulus between the casing and the earth formation. The measurement obtained by these tools is based on a pulse echo technique, whereby a single transducer, pulsed with a broad-band signal (ie., 200–600 kHz), insonifies the casing at near-normal incidence, and receives reflected echoes. The method of measurement is based on exciting a casing resonance, measuring the temporal period and amplitude decay rate, and interpreting the data to determine whether cement or undisplaced mud lies adjacent to the casing. Such ultrasonic techniques, optimized to yield information about casing thickness, are described in U.S. Pat. No. 2,538,114 to Mason and U.S. Pat. No. 4,255,798 to Havira. The main limitation of these pulse echo techniques is that little of the acoustic energy (i.e., typically less than 10 percent) is transmitted through the casing to probe the annulus.

U.S. Pat. No. 5,011,676 to Broding purports to address the problem of primary and multiple reflections from a well casing interfering with formation reflection signals. Broding suggests elimination of interfering casing reflections by using one or several acoustic transducers directed on the casing at incident angles that fall between the compressional and shear critical angles of (borehole fluid)-steel interface. such that only shear waves are excited within the casing and no compressional waves propagate therein. The method relies on the fact that no signal is received so long as the cement-casing interface is regular, the annulus contains no channels or discontinuities, and the cement-formation interface is also smooth. Hence, when a signal is received by the transducer, one or more than one of these conditions is violated. And Broding does not offer a methodology on how to relate the received signal to the scatterer responsible for establishing it. Moreover, the Broding disclosure also states that when the transducer energy is directed at an angle larger than the shear critical angle, no energy is transmitted through the casing and into the annulus. Applicant herein has found this to be incorrect.

EP 0549 419 B1 to Stanke et al. disclose a method and apparatus to determine hydraulic isolation of oilfield casings by considering the entire volume of the annulus between the casing and the earth formation, and characterizing the third interface formed at the juncture of a second material, contacting the outside of the casing, and a third material adjacent to, and outside, the second material. Interrogation of the "third interface" is performed by directing an acoustic pulse at a segment of the casing. Ultrasonic transducers aligned along the casing axis—at angles of incidence, with respect to the casing inner wall, falling within the compressional and shear critical angles of a water-steel interface, i.e., about 14 to 27 degrees—such that shear signals within the casing are optimized and compressional signals within the casing are excluded. To effectively track a third-interface echo as the annulus thickness varies, a receiver array and complex signal processing algorithm are required. Additionally, the measurement would be adversely affected in attenuative muds.

In light of the above, one object of the present invention is a method and apparatus for ultrasonically imaging cased wells which overcomes one or more of the above-noted disadvantages of traditional approaches.

SUMMARY OF THE INVENTION

Generally speaking, and without intending to be limiting, one aspect of the invention relates to method(s) for analyzing, imaging, or characterizing cased wells, such as, for example, a method comprising the following: (i) exciting a flexural wave in a casing by insonifying the casing with a pulsed, collimated acoustic excitation aligned at an angle greater than the shear critical angle of the fluid-casing interface; (ii) receiving one or more echoes, (iii) analyzing the echoes to characterize the cased well; and, optionally, (iv) providing an image of at least a portion of the cased well. Additionally, the invention may also involve: (iv) identifying a scatterer in the annulus or a feature of the formation wall; (v) utilizing an inversion method to derive a footprint for a probing beam directed toward said scatterer or feature; and (vi) utilizing information from (v) to obtain more accurate information about the size of said scatterer or feature. Still further, the invention may also involve: (iv) providing a 3D image of scatterers in the annulus and/or features of the formation wall and (v) zooming the 3D image in accordance with instructions from a user; or (iv) providing a 3D image of scatterers in the annulus and/or features of the formation wall and (v) reforming the 3D image to focus on a specific region of 3D space.

Moreover, in accordance with another general aspect of the invention, and, again, not intending to be limiting, "analyzing the echoes" may include one or more of the following: (a) analyzing the propagation time of the echoes to determine the location of scatterers within the annulus; (b) analyzing the amplitude of envelopes of the echoes to determine an approximation of the azimuthal and axial size of scatterers within the annulus; (c) analyzing the positive and/or negative peak amplitudes of echoes to determine the impedance of scatterers within the annulus; (d) determining whether the scatterers are fluid-filled channels or gas-filled channels; (e) analyzing the propagation time of echoes from the formation wall to determine hole diameter; (f) analyzing the propagation time of echoes from the formation wall to determine casing eccentricity; (g) analyzing the propagation time of echoes from the formation wall to determine wave speeds in the cement, and analyzing such wave,speed information to obtain information about cement mechanical properties; (h) analyzing the amplitude of echoes from the formation wall to detect and/or identify fractures and/or faults intersecting the borehole; (i) analyzing the amplitude and propagation time of echoes from the formation wall to detect and/or identify enlargements of the borehole diameter associated with breakouts, washouts, and/or cavities; (j) analyzing the positive and/or negative peak amplitude of echoes from the formation wall to detect and/or identify dipping beds in the formation; (k) utilizing an inversion method in which information about early-arriving echoes due to propagation in the casing is used to approximate the profiles of the energy transmitted into the annulus; (l) using these profiles to construct the profile of a probing beam that gives rise to the echoes originating in the annulus and at the formation wall, and utilizing an inversion method in conjunction with the profile of the probing beam to extract from the amplitude of the third-interface echo(es) the size of scatter(s) in the annulus and/or fractures on the formation wall; (m) analyzing early-arriving echoes to qualitatively evaluate the casing for corrosion and/or perforations; (n) analyzing early-arriving echoes to detect the presence of gas-like material at the casing-cement interface; (o) determining whether the early-arriving echoes resemble a time elongated wave-train (e.g., a ringing echo) and, if so, indicating the presence of gas-like material at the casing-cement interface; (p) analyzing the echoes to provide a qualitative indication of cement strength; (q) analyzing early-arriving echoes to extract their dispersion characteristics; (r) determining casing thickness from the dispersion characteristics; (s) determining casing metal loss from said casing thickness information; (t) processing echoes arriving after the early-arriving echoes to determine their multiplicity for qualitative determination of cement strength; (u) processing echoes arriving after the early-arriving echoes to determine their propagation time inside the cement; and/or, (v) processing echoes arriving after the early-arriving echoes to determine whether they arose from scatterers in the annulus or at the formation wall.

Again, generally speaking, and without intending to be limiting, flexural wave excitation may be achieved by insonifying the casing with a pulsed, collimated acoustic excitation aligned at an angle greater than the shear critical angle of the fluid-casing interface (about 25–29 degrees), or by any other method of creating a substantial, predominantly, or prevailingly flexural excitation in the casing.

Yet again, generally speaking, and without intending to be limiting, a still further aspect of the invention relates to an apparatus for inspecting, imaging, analyzing, or characterizing cased wells, such as, for example, an apparatus comprising the following: (i) means (of any type whatsoever) for exciting a flexural wave in a casing by insonifying the casing with a pulsed, collimated acoustic excitation aligned at an angle greater than the shear critical angle of the fluid-casing interface; (ii) means (of any type) for receiving one or more echoes; (iii) means (of any type) for analyzing the echoes to characterize the cased well; and, optionally, (iv) means (of any type) for providing an image of at least a portion of the cased well; or, optionally, (iv) means (of any type) for identifying a scatterer in the annulus or a feature of the formation wall; (v) means (of any type) for utilizing an inversion method to derive a footprint for a probing beam directed toward said scatterer or feature; and, (vi) means (of any type) for utilizing information from (v) to obtain more accurate information about the size of said scatterer or feature; or, optionally, (iv) means (of any type) for providing a 3D image of scatterers in the annulus and/or features of the formation wall; and, (v) means (of any type) for zooming the 3D image in accordance with instructions from a user; or, optionally, (iv) means (of any type) for providing a 3D image of scatterers in the annulus and/or features of the formation wall; and, (v) means (of any type) for reforming said 3D image to focus on a specific region of 3D space.

Furthermore, in accordance with still further aspects of the invention, and, again, not intending to be limiting, "means for analyzing the echoes" may include one or more of the following: (a) means (of any type) for analyzing the propagation time of the echoes to determine the location of scatterers within the annulus; (b) means (of any type) for analyzing the amplitude of envelopes of the echoes to determine an approximation of the azimuthal and axial size of scatterers within the annulus; (c) means (of any type) for analyzing the positive and/or negative peak amplitudes of echoes to determine the impedance of scatterers within the annulus (d) means (of any type) for determining whether the scatterers are fluid-filled channels or gas-filled channels; (e) means (of any type) for analyzing the propagation time of echoes from the formation wall to determine hole diameter; (f) means (of any type) for analyzing the propagation time of echoes from the formation wall to determine casing eccentricity; (g) means (of any type) for analyzing the propagation time of echoes from the formation wall to determine wave speeds in the cement and for using such information to compute information about mechanical properties of the cement; (h) means (of any type) for analyzing the amplitude of echoes from the formation wall to detect and/or identify fractures and/or faults intersecting the borehole; (i) means (of any type) for analyzing the amplitude and propagation time of echoes from the formation wall to detect and/or identify enlargements of the borehole diameter associated with breakouts, washouts, and/or cavities; (j) means (of any type) for analyzing the positive and/or negative peak amplitude of echoes from the formation wall to detect and/or identify dipping beds in the formation; (k) means (of any type) for utilizing an inversion method in which information about early-arriving echoes due to propagation in the casing is used to approximate the profiles of the energy transmitted into the annulus; (l) means (of any type) for using the profiles to construct the profile of a probing beam that gives rise to the echoes originating in the annulus and at the formation wall; (m) means (of any type) for analyzing early-arriving echoes to qualitatively evaluate the casing for corrosion and/or perforations; (n) means (of any type) for analyzing early-arriving echoes to detect the presence of gas-like material at the casing-cement interface; (o) means (of any type) for determining whether the early-arriving echoes resemble a time-elongated wave-train and, if so, indicating the presence of gas-like material at the casing-cement interface; (p) means (of any type) for analyzing the echoes to provide a qualitative indication of cement strength; (q) means (of any type) for analyzing early-arriving echoes to extract their dispersion characteristics; (r) means (of any type) for determining casing thickness from the dispersion characteristics; (s) means (of any type) for determining casing metal loss from said casing thickness information; (t) means (of any type) for processing echoes arriving after the early-arriving echoes to determine their multiplicity for qualitative determination of cement strength; (u) means (of any type) for processing echoes arriving after the early-arriving echoes to determine their propagation time inside the cement; and/or, (v) means (of any type) for processing echoes arriving after the early-arriving echoes to determine whether they arose from scatterers in the annulus or at the formation wall.

The above-referred to excitations may be created by single or multiple transmitting elements Similarly the above-referred to echoes may be received by single or multiple receiving elements.

The invention is preferably practiced using a combined apparatus (such as a sonde, or drill-string section) containing at least one excitation device and one receiving device. Such combined apparatus may be disposed (and vertically positioned) in a borehole by a wireline, by coiled tubing, as part of a drill-string, or by a robotic apparatus, and is preferably rotatable about the axis of the borehole to provide azimuthal information. Alternatively, azimuthal information may be obtained via a plurality of transmitter(s) and/or receiver(s) positioned concentrically about the axis of the borehole.

BRIEF DESCRIPTION OF THE DRAWINGS

Certain features and advantages of the present invention will become apparent from the accompanying set of drawings, in which.

It is to be understood that the drawings are to be used for the purpose of illustration only, and not as a definition of the metes and bounds of the invention, or as a basis for reading non-existent or unrecited limitations into the claims.

DESCRIPTION OF THE PREFERRED EMBODIMENT(S)

Figure 1:
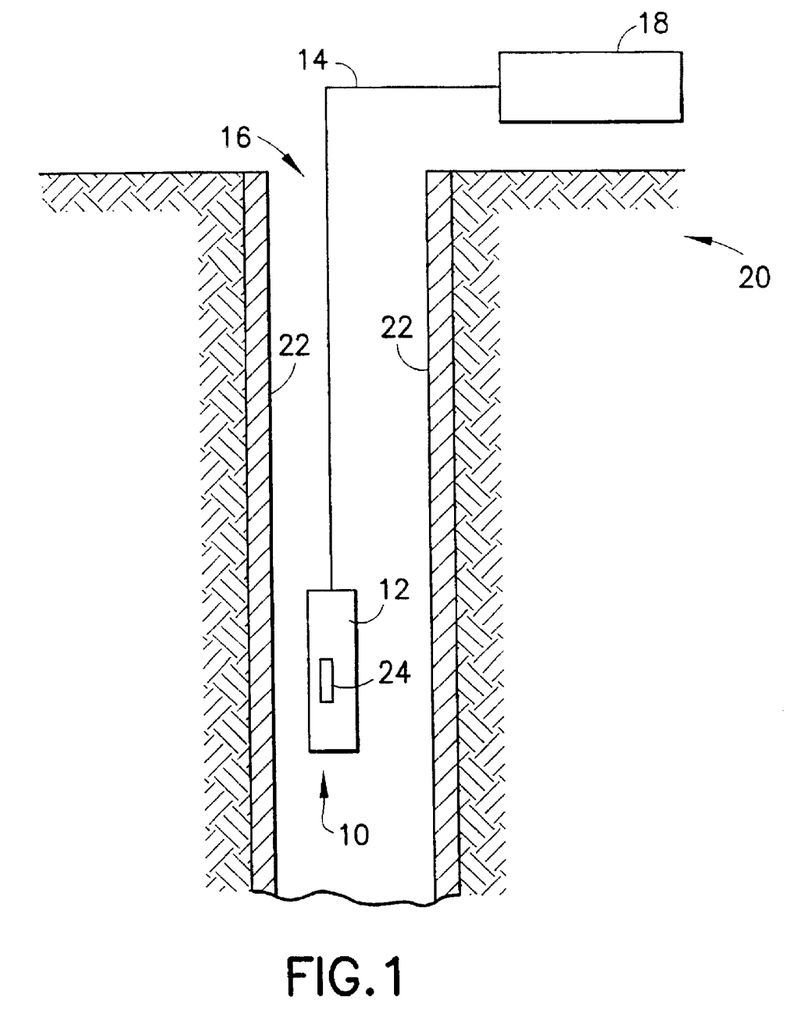
FIG. 1 is a schematic diagram of a logging operation.

Referring first to FIG. 1, which shows a schematic diagram of a logging operation, a sonde 10 (which may be self-contained, or part of drill string or other apparatus) for acquiring acoustic data includes a pressure-resistant housing 12 suspended by armored multi-conductor cable 14 (or coiled tubing or other means of conveyance) in a borehole 16. Cable 14 comprises conductors that electrically connect equipment within housing 12 with a data processing system 18, preferably located at the surface. A winch (not shown) is located at the surface and uses the cable 14 to lower and raise sonde 10 in the borehole, thereby traversing the earth formation 20.

Sonde 10 acquires acoustic data by emitting an acoustic pulse into casing 22 and detecting a reflected waveform. An apparatus 24 according to this invention comprises at least one detector and at least one transmitter. The transmitter produces a pulse upon excitation. The pulse is directed into casing 22, and a resulting return signal is detected by the receiver. The return waveforms are analyzed by the data processing system 18. Many techniques for analysis of acoustic waveforms are known in the art. One particularly useful technique is "bin processing"—as described in U.S. Pat. No. 5,859,811 to Miller and Stanke, which is incorporated herein by reference.

Figure 2:
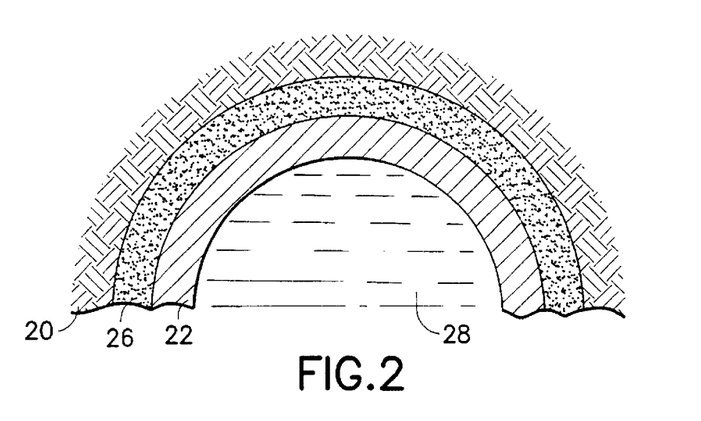
FIG. 2 is a cross-sectional diagram showing materials used in a completed borehole to achieve cementation for hydraulic isolation.

FIG. 2 is a cross-sectional diagram showing materials used in a completed borehole to achieve cementation for hydraulic isolation. The borehole 16 is cased with a first material, typically steel pipe 22. Outside, and adjacent to, the first material 22 lies a second material 26. This second material is typically a fill material, commonly referred to as cement, which is pumped into the annulus between casing 22 and the formation 20. The cement hydrates to retain casing 22 rigidly in position. More importantly. the cement is expected to completely fill the annulus between casing 22 and formation 20, thereby sealing off the hydrocarbon strata from the other layers. The cement displaces the borehole fluid, usually in the form of mud, which remains inside casing 22. When the well starts producing hydrocarbons, production fluids (oil, water, and gas) fill the inside of casing 22.

Figure 3:
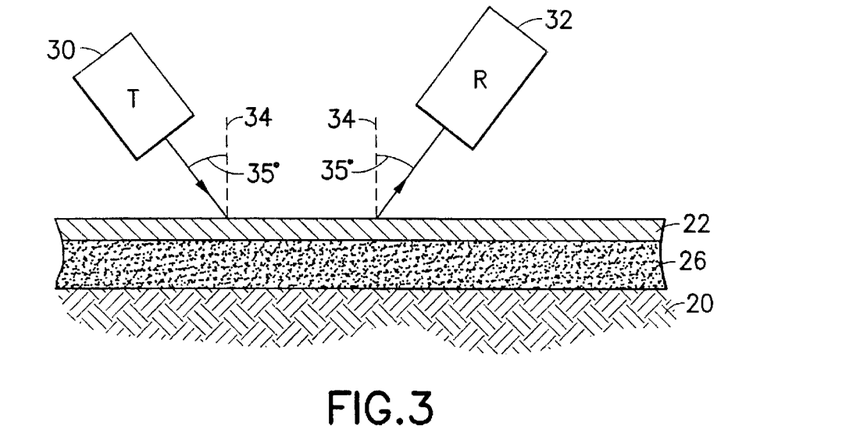
FIG. 3 illustrates a transmitter and receiver positioned to operate in accordance with the present invention.

FIG. 3 illustrates a transmitter 30 and receiver 32 of apparatus 24 mounted in the housing 12 of sonde 10. Transmitter 30 is spaced apart from receiver 32. The transducers 30, 32 are aligned at an angle 35 (measured with respect to the casing normal 34) larger than the shear critical angle of a fluid-steel interface. (The shear critical angle for fresh water-steel is approximately 27 degrees; salt water-steel is approximately 29 degrees; and oil-steel is approximately 25 degrees.) By aligning the transducers 30, 32 at angles larger than the shear critical angle for the fluid-steel interface, a flexural wave is excited in the casing. It then propagates inside the casing 22 and sheds energy to the surrounding borehole fluid 28 and annulus 26.

(Those skilled in the art will appreciate that the invention may be alternatively implemented using one or more transducers, configured in the manner disclosed in U.S. Pat. No. 5,001,676 to Broding, which is incorporated herein by reference.)

Figure 4:
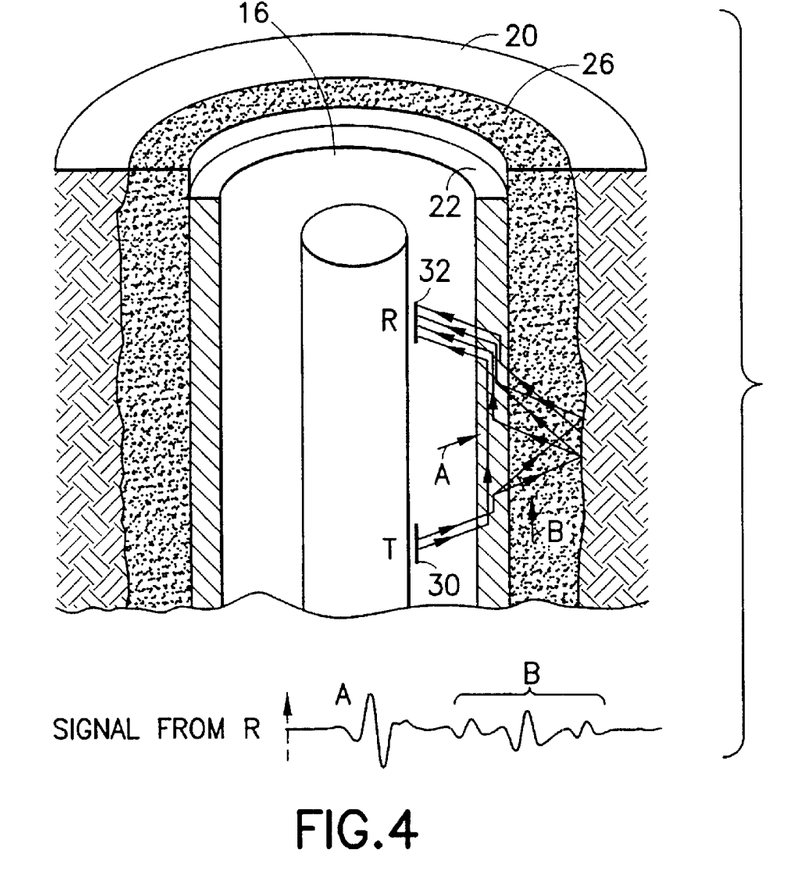
FIG. 4 shows a plurality of exemplary paths traversed by an excitation in a cased well along with an exemplary waveform that results from such propagation.

FIG. 4 shows a plurality of exemplary paths traversed by an excitation emanating from transmitter 30 and received by receiver 32, along with an exemplary waveform (received at receiver 32) that results from such propagation. The received waveform typically consists of a compact casing arrival (depicted by A) followed by well resolvable third-interface echo(es) (depicted by B).

The number of third-interface echoes detected could be one or more than one, depending on the properties of the cement and on the presence and size of inhomogineities in the annulus.

Without presence of an inhomogeneity, the third-interface echo is multiple if the cement is soft or moderate in strength, and single if the cement is hard in strength.

When the cement is soft or moderate, both compressional (P) and shear (S) waves propagate inside the cemented annulus, hence giving rise to P to P, P to S, S to P, and S to S wave specular reflections at the annulus-formation interface, which are detected by the receiver in the borehole. When the cement is hard, only shear waves can propagate, giving rise to S to S specular reflection echo at the annulus-formation interface.

In presence of an inhomogeneity of much smaller axial (i.e., along the casing cylindrical axis) extent than the spacing between the transmitter and receiver, the receiver may detect multiple third-interface echoes arising from the annulus-inhomogeneity and annulus-formation interfaces.

If the inhomogeneity axial extent is large, then the number of third-interface echoes arising at the annulus-inhomogeneity interface depend on the cement properties, as in the case with no inhomogeneity.

In case the annulus is filled with a fluid, only compressional waves propagate in the annulus. It is expected that a single third-interface echo is detected under typical conditions of good annulus cementation with a hard-strength cement, and more-than-one third-interface echo (PP and PS/SP in general) is detected under typical conditions of good annulus cementation with a light-weight cement. The invention is also effective in the presence of a fluid-filled microannulus. In such case, the amplitude of the casing arrival and third-interface echo(es) may he different from the case where a microannulus is absent.

In a preferred embodiment of the subject invention, signals detected by the receiver 32 furnish, from the transit times and amplitudes of the casing arrival and annulus/formation wall reflection echoes, quantitative information about the casing, the annulus fill, and cement-formation interface. The transit time of the casing arrival depends primarily on the T-R spacing and tool-casing standoff.

As the flexural wave propagates along the casing, its amplitude decays exponentially with a rate that depends on the casing thickness, the casing-cement bond condition, and the cement acoustic properties. The time delays of the annulus/formation echoes, with respect to the casing arrival, depend on the cement compressional and shear wave speeds and annulus thickness or position of the scatterers that give rise to the echoes. The amplitude of the annulus/formation echoes depend on the flexural decay rate. the T-R spacing, the cement wave speeds and attenuation, and the reflectivity of the cement/formation or cement/scatterer interface. The transit times of the casing arrival and of the third-interface echoes can be used to derive the annulus thickness and the location of a scatterer or, alternatively, the cement wave speeds.

Indeed, those skilled in the art of subterranean acoustic processing will appreciate that a variety of analytical techniques can be used in combination with the method(s)/apparatus of the invention to provide useful characterizations of cased wells. Such techniques include, but are not limited to, the following: (a) analyzing the propagation time of the echoes to determine the location of scatterers within the annulus; (b) analyzing the amplitude of envelopes of the echoes to determine an approximation of the azimuthal and axial size of scatterers within the annulus; (c) analyzing the positive and/or negative peak amplitudes of echoes to determine the impedance of scatterers within the annulus; (d) determining whether the scatterers are fluid-filled channels or gas-filled channels; (e) analyzing the propagation time of echoes from the formation wall to determine hole diameter; (f) analyzing the propagation time of echoes from the formation wall to determine casing eccentricity; (g) analyzing the propagation time of echoes from the formation wall to determine wave speeds in the cement; (h) analyzing the amplitude of echoes from the formation wall to detect and/or identify fractures and/or faults intersecting the borehole; (i) analyzing the amplitude and propagation time of echoes from the formation wall to detect and/or identify enlargements of the borehole diameter associated with breakouts, washouts, and/or cavities; (j) analyzing the positive and/or negative peak amplitude of echoes from the formation wall to detect and/or identify dipping beds in the formation; (k) utilizing an inversion method in which information about early-arriving echoes due to propagation in the casing is used to approximate the profiles of the energy transmitted into the annulus; (l) using these profiles to construct the profile of a probing beam that gives rise to the echoes originating in the annulus and at the formation wall, and utilizing and inversion method in conjunction with the profile of the probing beam to extract from the amplitude of the third-interface echo(es) the size of the scatterers in the annulus and/or features of the formation wall; (m) analyzing early arriving echoes to qualitatively evaluate the casing for corrosion and/or perforations; (n) analyzing early-arriving echoes to detect the presence of gas-like material at the casing-cement interface; (o) determining whether the early-arriving echoes resemble a time-elongated wave-train and, if so, indicating the presence of gas-like material at the casing-cement interface; (p) analyzing the echoes to provide a qualitative indication of cement strength; (q) analyzing early-arriving echoes to extract their dispersion characteristics; (r) determining casing thickness from the dispersion characteristics; (s) determining casing metal loss from said casing thickness information; (t) processing echoes arriving after the early-arriving echoes to determine their multiplicity for qualitative determination of cement strength; (u) processing echoes arriving after the early-arriving echoes to determine their propagation time inside the cement; and/or, (v) processing echoes arriving after the early-arriving echoes to determine whether they arose from scatterers in the annulus or at the formation wall.

The foregoing description of the preferred and alternate embodiments of the present invention have been presented for purposes of illustration and description. It is not intended to be exhaustive or limit the invention to the precise form disclosed. Obviously, many modifications and variations will be apparent to those skilled in the art. For example, the technique may be used to image features on the formation wall, such as breakouts and sanding zones, characterized by diameter enlargement. Also, the technique can detect the location of a channel within the annulus. And the technique is also useful for imaging fractures and/or faults that intersect the borehole, and dipping beds.

Thus, while the foregoing has described aspects of various embodiments of the present invention. those skilled in the art will recognize that alternative elements and techniques, and/or combinations and permutations of the described elements and techniques, can be substituted for, or added to, the embodiments and methods described herein. It is intended, therefore, that the present invention not be defined by the specific embodiments and methods described herein, but rather by the appended claims, which are intended to be construed in accordance with the following well-settled principles of claim construction:

Each claim should be given its broadest reasonable interpretation consistent with the specification.

Limitations should not be read from the specification or drawings into the claims (e.g., if the claim calls for a "chair," and the specification and drawings show a rocking chair, the claim term "chair" should not be limited to a rocking chair, but rather should be construed to cover any type of "chair").

The words "comprising," "including," and "having" are always open-ended, irrespective of whether they appear as the primary transitional phrase of a claim or as a transitional phrase within an element or sub-element of the claim (e.g., the claim "a widget comprising: A; B; and C" would be infringed by a device containing 2A's, B, and 3C's; also, the claim "a gizmo comprising: A; B; including X, Y, and Z; and C, having P and Q" would be infringed by a device containing 3A's, 2X's, 3Y's, Z, 6P's, and Q).

The indefinite articles "a" "an" mean "one or more"; where, instead, a purely singular meaning is intended, a phrase such as "one," "only one," or "a single," will appear.

Descriptive matter which appears only in the preamble portion of a claim is not to be considered a limitation of the claim.

Words in a claim should be given their plain, ordinary, and generic meaning, unless it is readily apparent from the specification that an unusual meaning was intended.

Where the phrase "means for" appears in a claim limitation, it is intended that the limitation be construed in accordance with 35 U.S.C. §112 ¶6; conversely, an absence of the specific words "means for" connotes an intent that the "plain meaning" rule. rather than §112 ¶6, be used in construing the limitation.

Where the phrase "means for" precedes a data processing or manipulation "function," it is intended that the resulting means-plus-function element be construed to cover any, and all, computer implementation(s) of the recited "function."

A claim that contains more than one computer-implemented means-plus-function element should not be construed to require that each means-plus-function element must be a structurally distinct entity (such as a particular piece of hardware or block of code): rather, such claim should be construed merely to require that the overall combination of hardware/software which implements the invention must, as a whole, implement at least the function(s) called for by the claim's means-plus-function element(s).

A means-plus-function element should be construed to require only the "function" specifically articulated in the claim, and not in a way that requires additional "functions" or "functional limitations" described in the specification or performed in the preferred embodiment (s).

In accordance with O.I. Corp. v. Tekmar Co., 42 USPQ2d 1777, 1782 (Fed. Cir. 1997), "a statement in a preamble of a result that necessarily follows from performing a series of steps does not convert each of those steps into step-plus-function clauses."

The existence of method claims that parallel a set of means-plus-function apparatus claims does not mean, or suggest, that the method claims should be construed under 35 U.S.C. §112 ¶6. See Tekmar, 42 USPQ2d at 1782 ("Each claim must be independently reviewed in order to determine if it is subject to the requirements of section 112, Para. 6. Interpretation of claims would be confusing indeed if claims that are not means- or step-plus-function claims were to be interpreted as if they were, only because they use language similar to that used in other claims that are subject to this provision.").

The step-plus-function provision of 35 U.S.C. §112 ¶6 does not apply to a limitation that recites an "act," rather than a "function." See Serrano v. Telular Corp., 42 USPQ2d 1538, 1542 (Fed. Cir. 1997). As used in the claims below, the verbs "excite," "insonify," "receive," "analyze," "provide," "determine," "detect," "identify," "utilize," "approximate," "construct," "obtain," "zoom," "reform," "evaluate," "indicate," "extract," "process," and "create" are intended to describe acts, rather than functions or steps.

A means-plus-function limitation should never be construed as limited solely to the structure(s) described in the specification. See D.M.I., Inc. v. Deere & Co., 225 USPQ 236, 238 (Fed. Cir. 1985)("The statute, §112–6, was written precisely to avoid a holding that a means-plus-function limitation must be read as covering only the means disclosed in the specification.").

Limitations from the narrow claims should not be "read into" the broad claims. See, e.g., Tandon Corp. v.

United States Int'l Trade Comm'n, 4 USPQ2d 1283, 1288 (Fed. Cir. 1987)("There is presumed to be a difference in meaning and Scope when different words or phrases are used in separate claims. To the extent that the absence of such difference in meaning and scope would make a claim superfluous, the doctrine of claim differentiation states the presumption that the difference between claims is significant.").

What is claimed is:

1. A method for characterizing a cased well, said cased well comprising a borehole drilled in a geological formation, a fluid-filled casing disposed in said borehole and cement disposed in an annulus between said casing and said formation, said method comprising:
   (i) exciting a flexural wave in said casing by insonifying said casing with a pulsed, collimated acoustic excitation aligned at an angle greater than the shear critical angle of the fluid-casing interface, said angle being measured with respect to the normal to the local interior wall of said casing;
   (ii) receiving one or more echoes; and,
   (iii) analyzing said echoes to characterize said cased well.

2. A method according to claim 1, further comprising:
   (iv) providing an image of at least a portion of the cased well.

3. A method according to claim 1, wherein step (iii) includes analyzing the propagation time of said echoes to determine the location of scatterers within the annulus.

4. A method according to claim 1, wherein step (iii) includes analyzing the amplitude of envelopes of the echoes to determine an approximation of the azimuthal and axial size of scatterers within the annulus.

5. A method according to claim 1, wherein step (iii) includes analyzing the positive and/or negative peak amplitudes of echoes to determine the impedance of scatterers within the annulus.

6. A method according to claim 5, wherein step (iii) further includes determining whether said scatterers are fluid-filled channels or gas-filled channels.

7. A method according to claim 1, wherein step (iii) includes analyzing the propagation time of echoes from the formation wall to determine hole diameter.

8. A method according to claim 1, wherein step (iii) includes analyzing the propagation time of echoes from the formation wall to determine casing eccentricity.

9. A method according to claim 1, wherein step (iii) includes analyzing the propagation time of echoes from the formation wall to determine wave speeds in the cement.

10. A method according to claim 1, wherein step (iii) includes analyzing the amplitude of echoes from the formation wall to detect and/or identify fractures or faults intersecting the borehole.

11. A method according to claim 1, wherein step (iii) includes analyzing the amplitude and propagation time of echoes from the formation wall to detect and/or identify enlargements of the borehole diameter associated with breakouts, washouts, and/or cavities.

12. A method according to claim 1, wherein step (iii) includes analyzing the positive and/or negative peak amplitude of echoes from the formation wall to detect and/or identify dipping beds in the formation.

13. A method according to claim 1, wherein step (iii) includes utilizing an inversion method in which information about early-arriving echoes due to propagation in the casing is used to approximate the profiles of the energy transmitted into the annulus.

14. A method according to claim 13, wherein said profiles are used to construct the profile of a probing beam that gives rise to the echoes originating in the annulus and at the formation wall.

15. A method according to claim 1, further comprising:
   (iv) identifying a scatterer in the annulus or a feature of the formation wall;
   (v) utilizing an inversion method to derive a footprint for a probing beam directed toward said scatterer or feature; and,
   (vi) utilizing information from step (v) to obtain more accurate information about the size of said scatterer or feature.

16. A method according to claim 1, further comprising:
   (iv) providing a 3D image of scatterers in the annulus and/or features of the formation wall;
   (v) zooming said 3D image in accordance with instructions from a user.

17. A method according to claim 1, further comprising:
   (iv) providing a 3D image of scatterers in the annulus and/or features of the formation wall;
   (v) reforming said 3D image to focus on a specific region of 3D space.

18. A method according to claim 1, wherein step (iii) includes analyzing early-arriving reflections to qualitatively evaluate the casing for corrosion and/or perforations.

19. A method according to claim 1, wherein step (iii) includes analyzing early-arriving echoes to detect the presence of gas-like material at the casing-cement interface.

20. A method according to claim 19, wherein step (iii) further includes determining whether said early-arriving echoes resemble a time-elongated wave-train and, if so, indicating the presence of gas-like material at the casing-cement interface.

21. A method according to claim 1, wherein step (iii) includes analyzing said echoes to provide a qualitative indication of cement strength.

22. A method according to claim 1, wherein step (iii) includes analyzing early-arriving echoes to extract their dispersion characteristics.

23. A method according to claim 22, wherein step (iii) further includes determining casing thickness from said dispersion characteristics.

24. A method according to claim 23, wherein step (iii) further includes determining casing metal loss from said casing thickness information.

25. A method according to claim 1, wherein step (iii) includes processing echoes arriving after the early-arriving echoes to determine their multiplicity for qualitative determination of cement strength.

26. A method according to claim 1, wherein step (iii) includes:
   processing echoes arriving after the early-arriving echoes to determine their propagation time inside the cement;
   utilizing an inversion method and said propagation time to determine wave speed in the cement and/or cement mechanical properties;
   providing a 3D image of wave speed and/or cement mechanical properties.

27. A method according to claim 1 wherein step (iii) includes processing echoes arriving after the early-arriving echoes to determine whether they arose from scatterers in the annulus or at the formation wall.

28. A method for characterizing a cased well, said cased well comprising a borehole drilled in a geological formation, a fluid-filled casing disposed inside said borehole, and a cement region disposed between said casing and said formation, said method comprising:

(i) exciting a flexural wave in said casing by insonifying said casing with a pulsed, collimated acoustic excitation aligned at an angle greater than about 25–29 degrees, said angle being measured with respect to the normal to the local interior wall of said casing;
(ii) receiving one or more echoes; and,
(iii) analyzing said echoes.

29. A method for imaging a cased well, comprising:
(i) exciting predominantly a flexural wave in a well casing;
(ii) receiving one or more echoes;
(iii) analyzing said echoes; and,
(iv) providing an image of at least of portion of said cased well.

30. A method for imaging a cased well, comprising:
(i) creating an excitation, consisting essentially of a flexural wave, in a well casing;
(ii) receiving one or more echoes;
(iii) analyzing said echoes; and,
(iv) providing an image of at least of portion of said cased well.

31. Apparatus for characterizing a cased well, said cased well comprising a borehole drilled in a geological formation, a fluid-filled casing disposed in said borehole and cement disposed in an annulus between said casing and said formation, said apparatus comprising:
means for insonifying said casing with a pulsed, collimated acoustic excitation aligned at an angle greater than the shear critical angle of the fluid-casing interface, said angle being measured with respect to the normal to the local interior wall of said casing;
means for receiving one or more echoes; and,
means for analyzing said echoes to characterize said cased well.

32. Apparatus according to claim 31, further comprising:
means for providing an image of at least a portion of the cased well.

33. Apparatus according to claim 31, further including means for analyzing the propagation time of said echoes to determine the location of scatterers within the annulus.

34. Apparatus according to claim 31, further including means for analyzing the amplitude of envelopes of the echoes to determine an approximation of the azimuthal and axial size of scatterers within the annulus.

35. Apparatus according to claim 31, further including means for analyzing the positive and/or negative peak amplitudes of echoes to determine the impedance of scatterers within the annulus.

36. Apparatus according to claim 35, further including means for determining whether said scatterers are fluid-filled channels or gas-filled channels.

37. Apparatus according to claim 31, further comprising means for analyzing the propagation time of echoes from the formation wall to determine hole diameter.

38. Apparatus according to claim 31, further comprising means for analyzing the propagation time of echoes from the formation wall to determine casing eccentricity.

39. Apparatus according to claim 31, further comprising means for analyzing the propagation time of echoes from the formation wall to determine wave speeds in the cement.

40. Apparatus according to claim 31, further comprising means for analyzing the amplitude of echoes from the formation wall to detect and/or identify fractures intersecting the borehole.

41. Apparatus according to claim 31, further comprising means for analyzing the amplitude and propagation time of echoes from the formation wall to detect and/or identify enlargements of the borehole diameter associated with breakouts, washouts, and/or cavities.

42. Apparatus according to claim 31, further comprising means for analyzing the positive and/or negative peak amplitude of echoes from the formation wall to detect and/or identify dipping beds in the formation.

43. Apparatus according to claim 31, further comprising means for utilizing an inversion method in which information about early-arriving echoes due to propagation in the casing is used to approximate the profiles of the energy transmitted into the annulus.

44. Apparatus according to claim 43, further comprising means for utilizing said profiles to construct the profile of a probing beam that gives rise to the echoes originating in the annulus and at the formation wall.

45. Apparatus according to claim 31, further comprising:
means for identifying a scatterer in the annulus or a feature of the formation wall;
means for utilizing an inversion method to derive a footprint for a probing beam directed toward said scatterer or feature; and,
means for utilizing information about said probing beam footprint to obtain more accurate information about the size of said scatterer or feature.

46. Apparatus according to claim 31, further comprising:
means for providing a 3D image of scatterers in the annulus and/or features of the formation wall; and,
means for zooming said 3D image in accordance with instructions from a user.

47. Apparatus according to claim 31, further comprising:
means for providing a 3D image of scatterers in the annulus and/or features of the formation wall;
means for reforming said 3D image to focus on a specific region of 3D space.

48. Apparatus according to claim 31, further comprising means for analyzing early-arriving reflections to qualitatively evaluate the casing for corrosion and/or perorations.

49. Apparatus according to claim 31, further comprising means for analyzing early-arriving echoes to detect the presence of gas-like material at the casing-cement interface.

50. Apparatus according to claim 49, further comprising means for determining whether said early-arriving echoes resemble a time-elongated wave-train and, if so, indicating the presence of gas-like material at the casing-cement interface.

51. Apparatus according to claim 31, further comprising means for analyzing said echoes to provide a qualitative indication of cement strength.

52. Apparatus according to claim 31, further comprising means for analyzing early-arriving echoes to extract their dispersion characteristics.

53. Apparatus according to claim 52, further comprising means for determining casing thickness from said dispersion characteristics.

54. Apparatus according to claim 53, further comprising means for determining casing metal loss from said casing thickness information.

55. Apparatus according to claim 31, further comprising means for processing echoes arriving after the early-arriving echoes to determine their multiplicity for qualitative determination of cement strength.

56. Apparatus according to claim 31, further comprising means for processing echoes arriving after the early-arriving echoes to determine their propagation time inside the cement.

57. Apparatus according to claim 31, further comprising means for processing echoes arriving after the early-arriving echoes to determine whether they arose from scatterers in the annulus or at the formation wall.

58. Apparatus for characterizing a cased well, comprising:
   at least one pulsed, collimated acoustic source, said source aligned at an angle greater than about 25–29 degrees with respect to the normal to a local interior wall of said well;
   at least one acoustic receiver; and,
   a computer programmed to analyze echoes received by the receiver.

59. Apparatus for imaging a cased well, comprising:
   means for exciting a predominantly flexural wave in a well casing;
   at least one receiver receiving one or more echoes;
   a computer analyzing said echoes; and,
   an output device providing an image of at least of portion of said cased well.

60. Apparatus for analyzing a cased well comprising:
   one or more sonic source(s) positioned to creating an excitation—consisting prevailingly of a flexural wave—in a well casing;
   one or more receiver(s) receiving echo(es); and,
   a computer analyzing said echo(es).

* * * * *